US009648874B2

(12) United States Patent
Topolkaraev et al.

(10) Patent No.: US 9,648,874 B2
(45) Date of Patent: *May 16, 2017

(54) NATURAL, MULTIPLE USE AND RE-USE, USER SATURATED WIPES

(75) Inventors: Vasily A. Topolkaraev, Appleton, WI (US); Neil T. Scholl, Neenah, WI (US); YoungSook Kim, YongIn-Si (KR); David W. Koenig, Menasha, WI (US); JaeHong Lee, YongIn-si (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 359 days.

This patent is subject to a terminal disclaimer.

(21) Appl. No.: 13/330,375

(22) Filed: Dec. 19, 2011

(65) Prior Publication Data
US 2013/0158128 A1    Jun. 20, 2013

Related U.S. Application Data

(63) Continuation-in-part of application No. 12/961,634, filed on Dec. 7, 2010, now Pat. No. 8,524,264, which is a continuation-in-part of application No. 12/961,638, filed on Dec. 7, 2010.

(51) Int. Cl.
*A01N 25/34* (2006.01)
*A01N 31/08* (2006.01)
*A61K 8/02* (2006.01)
*A01N 65/00* (2009.01)
*A01N 25/10* (2006.01)
*A01N 65/22* (2009.01)
*A61K 47/44* (2017.01)

(52) U.S. Cl.
CPC ............ *A01N 31/08* (2013.01); *A01N 25/10* (2013.01); *A01N 65/00* (2013.01); *A01N 65/22* (2013.01); *A61K 8/0208* (2013.01); *A61K 47/44* (2013.01)

(58) Field of Classification Search
CPC .............................. A61K 8/0208; A61K 47/44
USPC ......................................................... 424/402
See application file for complete search history.

(56) References Cited

U.S. PATENT DOCUMENTS

| 3,351,531 A | 11/1967 | Noznick et al. |
| 3,354,506 A | 11/1967 | Raley |
| 3,494,821 A | 2/1970 | Evans |
| 3,650,649 A | 3/1972 | Schippers |
| 3,801,429 A | 4/1974 | Schrenk et al. |
| 3,973,695 A | 8/1976 | Ames |
| 4,100,324 A | 7/1978 | Anderson et al. |
| 4,144,370 A | 3/1979 | Boulton |
| 4,232,047 A | 11/1980 | Sair et al. |
| 4,652,441 A | 3/1987 | Okada et al. |
| 4,690,825 A | 9/1987 | Won |
| 4,695,450 A | 9/1987 | Bauer et al. |
| 4,707,367 A | 11/1987 | Miller et al. |
| 4,820,435 A | 4/1989 | Zafiroglu |
| 5,023,080 A | 6/1991 | Gupta |
| 5,057,361 A | 10/1991 | Sayovitz et al. |
| 5,179,164 A | 1/1993 | Lausberg et al. |
| 5,240,764 A | 8/1993 | Haid et al. |
| 5,284,703 A | 2/1994 | Everhart et al. |
| 5,320,669 A | 6/1994 | Lim et al. |
| 5,330,768 A | 7/1994 | Park et al. |
| 5,350,624 A | 9/1994 | Georger et al. |
| 5,354,726 A | 10/1994 | Narayanan et al. |
| 5,380,530 A * | 1/1995 | Hill ............................ 424/440 |
| 5,395,055 A | 3/1995 | Shutov et al. |
| 5,397,834 A | 3/1995 | Jane et al. |
| 5,421,898 A | 6/1995 | Cavanagh |
| 5,523,293 A | 6/1996 | Jane et al. |
| 5,589,195 A | 12/1996 | Potter |
| 5,603,971 A | 2/1997 | Porzio et al. |
| 5,665,428 A | 9/1997 | Cha et al. |
| 5,687,875 A | 11/1997 | Watts et al. |
| 5,702,717 A | 12/1997 | Cha et al. |
| 5,723,588 A | 3/1998 | Donofrio et al. |
| 5,735,588 A | 4/1998 | Dittman et al. |
| 5,741,521 A | 4/1998 | Knight et al. |
| 5,785,179 A | 7/1998 | Buczwinski et al. |

(Continued)

FOREIGN PATENT DOCUMENTS

| CN | 1488290 A | 4/2004 |
| EP | 0 388 718 A2 | 9/1990 |

(Continued)

OTHER PUBLICATIONS

Co-pending U.S. Appl. No. 13/961,611, filed Dec. 7, 2010, by Lee et al. for "Wipe Coated with a Botanical Composition having Antimicrobial Properties."
Co-pending U.S. Appl. No. 12/961,619, filed Dec. 7, 2010, by Lee et al. for "Wipe Coated with a Botanical Emulsion having Antimicrobial Properties."
Co-pending U.S. Appl. No. 12/961,625, filed Dec. 7, 2010, by Topolkaraev et al. for "Melt-Blended Protein Composition."
Co-pending U.S. Appl. No. 12/961,634, filed Dec. 7, 2010, by Topolkaraev et al. for "Protein Stabilized Antimicrobial Composition Formed by Melt Processing."
Co-pending U.S. Appl. No. 12/961,638, filed Dec. 7, 2010, by Wang et al. for "Melt Processed Antimicrobial Composition."
Co-pending U.S. Appl. No. 13/330,406, filed Dec. 19, 2011, by Scholl et al. for "Natural, Multiple Release and Re-Use Compositions."

(Continued)

*Primary Examiner* — Ali Soroush
*Assistant Examiner* — Danielle Sullivan
(74) *Attorney, Agent, or Firm* — Kimberly-Clark Worldwide, Inc.

(57) ABSTRACT

The present invention relates to a wipe suitable for multiple re-use comprising a biopolymer matrix composition, said biopolymer matrix comprising from about 0.1% to about 40% of an essential oil, about 30% to about 95% of a biopolymer, and about 1% to about 50% of a carrier fluid wherein a limited amount of said essential oil can be released from said matrix composition when exposed to a liquid solution; and wherein an additional limited amount of said essential oil can be re-released repetitiously thereafter upon re-use with an additional exposure of a liquid solution to said wipe.

12 Claims, No Drawings

(56) References Cited

U.S. PATENT DOCUMENTS

| | | | |
|---|---|---|---|
| 5,871,872 A | 2/1999 | Matijevic et al. | |
| 5,882,702 A | 3/1999 | Abdel-Malik et al. | |
| 5,919,471 A | 7/1999 | Saferstein et al. | |
| 5,928,661 A | 7/1999 | Fujita et al. | |
| 5,964,351 A | 10/1999 | Zander | |
| 6,030,331 A | 2/2000 | Zander | |
| 6,090,925 A | 7/2000 | Woiszwillo et al. | |
| 6,121,165 A | 9/2000 | Mackey et al. | |
| 6,133,166 A | 10/2000 | Nissing et al. | |
| 6,158,614 A | 12/2000 | Haines et al. | |
| 6,238,682 B1 | 5/2001 | Klofta et al. | |
| 6,269,969 B1 | 8/2001 | Huang et al. | |
| 6,269,970 B1 | 8/2001 | Huang et al. | |
| 6,270,878 B1 | 8/2001 | Wegele et al. | |
| 6,273,359 B1 | 8/2001 | Newman et al. | |
| 6,280,758 B1* | 8/2001 | Warren | A61K 8/0208 424/400 |
| 6,315,864 B2 | 11/2001 | Anderson et al. | |
| 6,523,690 B1 | 2/2003 | Buck et al. | |
| 6,568,625 B2 | 5/2003 | Faulks et al. | |
| 6,589,549 B2 | 7/2003 | Shih et al. | |
| 6,680,287 B2 | 1/2004 | Wisniewski et al. | |
| 6,719,995 B2 | 4/2004 | Rajaiah et al. | |
| 6,766,919 B2 | 7/2004 | Huang et al. | |
| 6,770,433 B2 | 8/2004 | Hioki | |
| 6,806,213 B2 | 10/2004 | Brooks | |
| 6,806,353 B2 | 10/2004 | Zhang et al. | |
| 6,824,734 B2 | 11/2004 | Boggs et al. | |
| 6,989,149 B2 | 1/2006 | Glenn, Jr. et al. | |
| 7,127,771 B2* | 10/2006 | McDevitt et al. | 15/227 |
| 7,250,152 B2 | 7/2007 | Gentile et al. | |
| 7,338,927 B2 | 3/2008 | Shapiro | |
| 7,462,348 B2 | 12/2008 | Gruenbacher et al. | |
| 7,488,503 B1 | 2/2009 | Porzio et al. | |
| 7,560,422 B2 | 7/2009 | Shapiro | |
| 7,605,096 B2 | 10/2009 | Tomarchio et al. | |
| 7,612,029 B2 | 11/2009 | Foland et al. | |
| 7,614,812 B2 | 11/2009 | Reddy et al. | |
| 7,662,409 B2 | 2/2010 | Masters | |
| 7,803,413 B2 | 9/2010 | Van Lengerich et al. | |
| 7,803,414 B2 | 9/2010 | Van Lengerich et al. | |
| 7,998,888 B2 | 8/2011 | Shi et al. | |
| 2002/0160035 A1 | 10/2002 | Fotinos | |
| 2003/0008008 A1* | 1/2003 | Leung et al. | 424/486 |
| 2003/0031722 A1 | 2/2003 | Cao et al. | |
| 2003/0082219 A1 | 5/2003 | Warren et al. | |
| 2003/0105207 A1 | 6/2003 | Kleyer et al. | |
| 2003/0135172 A1 | 7/2003 | Whitmore et al. | |
| 2003/0206942 A1 | 11/2003 | Kulkarni et al. | |
| 2004/0018241 A1 | 1/2004 | Houze et al. | |
| 2004/0026289 A1 | 2/2004 | Halkyard | |
| 2004/0037870 A9 | 2/2004 | Fotinos | |
| 2004/0043134 A1 | 3/2004 | Corriveau et al. | |
| 2004/0180110 A1* | 9/2004 | Mistry | 426/3 |
| 2004/0234609 A1 | 11/2004 | Collier et al. | |
| 2004/0255408 A1 | 12/2004 | Norton et al. | |
| 2005/0048121 A1 | 3/2005 | East et al. | |
| 2005/0158369 A1 | 7/2005 | Dorschner et al. | |
| 2005/0197319 A1 | 9/2005 | Nonomura et al. | |
| 2005/0214349 A1 | 9/2005 | Nie et al. | |
| 2005/0238591 A1 | 10/2005 | Sagel et al. | |
| 2005/0245162 A1 | 11/2005 | McCormack et al. | |
| 2006/0062832 A1 | 3/2006 | Lopes | |
| 2006/0128248 A1 | 6/2006 | Ellis | |
| 2007/0042182 A1 | 2/2007 | Markus et al. | |
| 2007/0077281 A1 | 4/2007 | Theobald et al. | |
| 2007/0224261 A1 | 9/2007 | Draper | |
| 2007/0254035 A1 | 11/2007 | Hao et al. | |
| 2007/0256247 A1 | 11/2007 | Privitera et al. | |
| 2007/0269567 A1 | 11/2007 | McMindes et al. | |
| 2008/0145426 A1 | 6/2008 | Amundson et al. | |
| 2008/0160084 A1 | 7/2008 | Huynh et al. | |
| 2008/0200359 A1 | 8/2008 | Smets et al. | |
| 2008/0207481 A1 | 8/2008 | Meine et al. | |
| 2008/0221003 A1 | 9/2008 | Meine et al. | |
| 2009/0087468 A1 | 4/2009 | Stephenson et al. | |
| 2009/0136555 A1 | 5/2009 | Crowley et al. | |
| 2009/0155447 A1 | 6/2009 | Moore et al. | |
| 2009/0175806 A1 | 7/2009 | Modak et al. | |
| 2009/0186096 A1 | 7/2009 | Kritzman et al. | |
| 2009/0196909 A1 | 8/2009 | Cooper et al. | |
| 2009/0226530 A1 | 9/2009 | Lassner et al. | |
| 2009/0232905 A1 | 9/2009 | Weiss et al. | |
| 2009/0286437 A1 | 11/2009 | Cunningham et al. | |
| 2009/0297664 A1 | 12/2009 | Forte et al. | |
| 2010/0034907 A1 | 2/2010 | Daigle et al. | |
| 2010/0065445 A1 | 3/2010 | Stevenson | |
| 2010/0101605 A1 | 4/2010 | Saint Victor | |
| 2010/0136201 A1 | 6/2010 | Bigeard et al. | |
| 2010/0144584 A1 | 6/2010 | Saint Victor | |
| 2010/0159170 A1* | 6/2010 | Wang et al. | 428/35.7 |
| 2010/0234517 A1 | 9/2010 | Plantenberg et al. | |
| 2010/0240724 A1 | 9/2010 | Chang et al. | |
| 2010/0240799 A1 | 9/2010 | Hofmann et al. | |
| 2010/0247371 A1 | 9/2010 | Farrugia et al. | |
| 2010/0272831 A1 | 10/2010 | Lagaron-Cabello et al. | |
| 2011/0086084 A1* | 4/2011 | Koenig et al. | 424/443 |
| 2011/0086085 A1 | 4/2011 | Wenzel et al. | |
| 2011/0150955 A1 | 6/2011 | Klingman | |
| 2011/0256199 A1 | 10/2011 | Zasypkin | |

FOREIGN PATENT DOCUMENTS

| | | |
|---|---|---|
| EP | 0 504 387 B1 | 7/1995 |
| EP | 1 004 703 A1 | 5/2000 |
| EP | 1 023 863 A1 | 8/2000 |
| EP | 1 059 032 A1 | 12/2000 |
| EP | 1 059 378 A1 | 12/2000 |
| EP | 1 275 370 A1 | 1/2003 |
| EP | 1 275 371 A1 | 1/2003 |
| EP | 0 863 942 B1 | 9/2003 |
| EP | 1 624 013 A1 | 2/2006 |
| EP | 1 618 240 B1 | 8/2006 |
| EP | 1716846 A2 | 11/2006 |
| EP | 1 408 926 B1 | 1/2007 |
| EP | 1 757 261 A2 | 2/2007 |
| EP | 1 867 317 A2 | 12/2007 |
| FR | 2 900 940 A1 | 11/2007 |
| GB | 2 444 112 A | 5/2008 |
| WO | WO 90/03784 A1 | 4/1990 |
| WO | WO 92/05708 A1 | 4/1992 |
| WO | WO 01/51557 A1 | 7/2001 |
| WO | WO 02/074430 A1 | 9/2002 |
| WO | WO 2004/019885 A2 | 3/2004 |
| WO | WO 2006/000032 A1 | 1/2006 |
| WO | WO 2007/135273 A2 | 11/2007 |
| WO | WO 2008/030969 A2 | 3/2008 |
| WO | WO 2008/063088 A1 | 5/2008 |
| WO | WO 2008/149232 A2 | 12/2008 |
| WO | WO 2009/079583 A1 | 6/2009 |
| WO | WO 2009/155115 A2 | 12/2009 |
| WO | WO 2010/022353 A1 | 2/2010 |
| WO | WO 2010/057658 A2 | 5/2010 |
| WO | WO 2012/077002 A2 | 6/2012 |
| WO | WO 2012/077006 A2 | 6/2012 |

OTHER PUBLICATIONS

American Society for Testing Materials (ASTM) Designation: D 445-04, "Standard Test Method for Kinematic Viscosity of Transparent and Opaque Liquids (and the Calculation of Dynamic Viscosity)," pp. 1-10, published Jun. 2004.

American Society for Testing Materials (ASTM) Designation: D5034-95, "Standard Test Method for Breaking Strength and Elongation of Textile Fabrics (Grab Test)," pp. 674-681, published Jul. 1995.

Auvergne et al., "Reactivity of Wheat Gluten Protein During Mechanical Mixing: Radical and Nucleophilic Reactions for the Addition of Molecules on Sulfur," *Biomacromolecules*, vol. 9, No. 2, Feb. 2008, pp. 664-671.

"Chemistry of Crosslinking," Thermo Fisher Scientific Inc., printed from Internet web site ,"www.piercenet.com", 2010, pp. 1-8.

(56) References Cited

OTHER PUBLICATIONS

Camire, Mary Ellen, "Protein Functionality Modification by Extrusion Cooking" (Presented at the 81st AOCS Annual Meeting, Baltimore, 1990), *JAOCS*, vol. 68, No. 3, Mar. 1991, pp. 200-205.
Del Nobile, M.A. et al., "Active Packaging by Extrusion Processing of Recyclable and Biodegradable Polymers," *Journal of Food Engineering*, vol. 93, 2009, pp. 1-6.
Del Nobile, M.A. et al., "Antimicrobial Efficacy and Release Kinetics of Thymol from Zein Films," *Journal of Food Engineering*, vol. 89, 2008, pp. 57-63.
Haw, Philip, "The HLB System—A Time Saving Guide to Surfactant Selection," Uniqema, presentation to the Midwest chapter of the Society of Cosmetic Chemists, Mar. 9, 2004, 39 pages.
Hu, Dingfei and Joel Coats, "Evaluation of the Environmental Fate of Thymol and Phenethyl Propionate in the Laboratory," *Pest Management Science*, vol. 64, Issue 7, Jul. 2008, pp. 775-779.
Kurniawan, Lusiana et al., "Chemical Modification of Wheat Protein-Based Natural Polymers: Grafting and Cross-Linking Reactions with Poly(ethylene oxide) Diglycidyl Ether and Ethyl Diamine," *Biomacromolecules*, published by American Chemical Society, vol. 8, No. 9, Sep. 2007, pp. 2909-2915.
Lawton, J.W. et al, "High-Temperature, Short-Time Extrusion of Wheat Gluten and a Bran-Like Fraction," *Cereal Chemistry*, American Association of Cereal Chemists, Inc., vol. 62, No. 4, 1985, pp. 267-271.
Liu, Wanjun et al., "Modifications of Soy Protein Plastic with Functional Monomer with Reactive Extrusion," *J. Polym. Environ.*, vol. 16, No. 3, 2008, pp. 177-182.
Mastromatteo, M. et al., "Controlled Release of Thymol from Zein Based Film," *Innovative Food Science and Emerging Technologies*, vol. 10, 2009, pp. 222-227.
O'Lenick Jr., Anthony J., "Silicone Emulsions and Surfactants—A Review," *Silicone Spectator*, 2009 (originally published May 2000), pp. 1-18.
Parris, Nicholas et al., "Encapsulation of Essential Oils in Zein Nanospherical Particles," *Journal of Agricultural and Food Chemistry*, vol. 53, No. 12, Jun. 15, 2005, pp. 4788-4792.
Redl, A. et al., "Extrusion of Wheat Gluten Plasticized With Glycerol: Influence of Process Conditions on Flow Behavior, Rheological Properties, and Molecular Size Distribution," *Cereal Chemistry*, vol. 76, No. 3, May-Jun. 1999, pp. 361-370.
Sanchez-Garcia, M.D. et al., "Novel Polycaprolactone Nanocomposites Containing Thymol of Interest in Antimicrobial Film and Coating Applications," *Journal of Plastic Film & Sheeting*, vol. 24, Jul.-Oct. 2008, pp. 239-251.
Ullsten, N. Henrik et al., "Enlarged Processing Window of Plasticized Wheat Gluten Using Salicylic Acid," *Biomacromolecules*, vol. 7, No. 3, Mar. 2006, pp. 771-776.
Vaz, Claudia M. et al., "Soy Matrix Drug Delivery System Obtained by Melt-Processing Techniques," *Biomacromolecules*, vol. 4, No. 6, Nov./Dec. 2003, pp. 1520-1529.
Verbeek, Casparus J.R. and Lisa E. van den Berg, "Extrusion Processing and Properties of Protein-Based Thermoplastics," *Macromolecular Materials and Engineering*, vol. 295, 2010, pp. 10-21.
Arfa, Afef Ben et al., "Coating Papers With Soy Protein Isolates as Inclusion Matrix of Carvacrol," Food Research International, vol. 40, 2007, pp. 22-32.
Chalier, Pascale et al., "Moisture and Temperature Triggered Release of a Volatile Active Agent from Soy Protein Coated Paper: Effect of Glass Transition Phenomena on Carvacrol Diffusion Coefficient," Journal of Agriculture and Food Chemistry, vol. 57, No. 2, Jan. 28, 2009, pp. 658-665.
Glenn, Gregory M. et al., Encapsulation of Plant Oils in Porous Starch Microspheres, Journal of Agricultural and Food Chemistry, vol. 58, No. 7, Apr. 14, 2010, pp. 4180-4184.
Hu, Chang-Ying et al., "Release of Thymol, Cinnamaldehyde and Vanillin from Soy Protein Isolate Films into Olive Oil," Packaging Technology and Science, vol. 25, No. 2, 2012, published online Aug. 21, 2011, pp. 97-106.
Kim, Y.D. et al., "Microencapsulation Properties of Gum Arabic and Several Food Proteins: Spray-Dried Orange Oil Emulsion Particles," Journal of Agricultural and Food Chemistry, American Chemical Society, vol. 44, No. 5, May 1, 1996, pp. 1314-1320.
Kuorwel, Kuorwel K. et al., Antimicrobial Activity of Natural Agents Coated on Starch-Based Films Against Staphylococcus Aureus, Journal of Food Science, vol. 76, No. 8, Oct. 19, 2011, pp. M531-M537.
Maier, H.G. et al., "Thermostabile Bindung von Aromastoffen an Staerke durch Extrudieren = Thermostable Binding of Aromatics on Starches by Extrusion," Lebensmittelchemie and Gerichtliche Chemie, vol. 41, No. 3, Jan. 1, 1987, pp. 56-59.
Maier, H.G. et al., "Thermostabile Bindung von Aromastoffen an Starke Teil 1: Bildung durch Gefriertrocken," Staerke—Starch, vol. 39, No. 4, Jan. 1, 1987, pp. 126-131.
Mascheroni, E. et al., "Anti-Microbial Effectiveness of Relative Humidity-Controlled Carvacrol Release from Wheat Gluten/Montmorillonite Coated Papers," Food Control, vol. 22, No. 10, Mar. 6, 2011, pp. 1582-1591.
Mascheroni, E. et al., "Designing of a Wheat Gluten/Montmorillonite Based System as Carvacrol Carrier: Rheological and Structural Properties," Food Hydrocolloids, vol. 24, No. 4, Jun. 1, 2010, pp. 406-413.
Meunier, J-P et al., "Use of Rotary Fluidized-Bed Technology for Development of Sustained-Release Plant Extract Pellets: Potential Application for Feed Additive Delivery," Journal of Animal Science, vol. 84, Jan. 1, 2006, pp. 1850-1859.
Mourtzinos, I. et al., "Encapsulation of Nutraceutical Monoterpenes in [beta]-Cyclodextrin and Modified Starch," Journal of Food Science, vol. 73, No. 1, Jan. 26, 2008, pp. S89-S94.
Oussalah, Mounia et al., "Inhibitory Effects of Selected Plant Essential Oils on the Growth of Four Pathogenic Bacteria: *E. Coli* 0157:H7, Salmonella Typhimurium, Staphylococcus Aureus and Listeria Monocytogenes," Food Control 18, 2007, pp. 414-420.
Snejdrova, Eva and Milan Dittrich, "Pharmaceutically Used Plasticizers," Chapter 3, Recent Advances in Plasticizers, Dr. Mohammad Luqman (Ed.), ISBN: 978-953-51/0363-9, InTech, Mar. 2012, pp. 45-68.
Tunc, S. et al., "Preparation of Active Antimicrobial Methyl Cellulose/Carvacrol/Montmorillonite Nanocomposite Films and Investigation of Carvacrol Release," Food Science and Technology, vol. 44, No. 2, Mar. 1, 2011, pp. 465-472.

\* cited by examiner

NATURAL, MULTIPLE USE AND RE-USE, USER SATURATED WIPES

CROSS REFERENCE TO RELATED APPLICATION

This application is a continuation-in-part of U.S. patent application Ser. No. 12/961,638 now U.S. Pat. No. 8,524,264 and Ser. No. 12/961,634 filed Dec. 7, 2010, the entirety of which is incorporated by reference herein.

FIELD OF THE INVENTION

The present invention relates to a substrate such as a wipe comprising an essential oil composition that provides a durable formulation that can be re-activated to create a wipe that can be repetitiously re-used over a number of times.

BACKGROUND OF THE INVENTION

Certain types of essential oils are known to be environmentally friendly and effective in providing a variety of benefits. The use of such oils in many commercial applications, however, has been limited due to their high volatility and instability in the presence of oxygen. Attempts to overcome this problem often involve the use of larger amounts of essential oils to prolong desired results. Unfortunately, this just leads to another problem in that simply incorporating higher concentrations of essential oils can lead to unintended and sometimes damaging results. Other attempts have involved the encapsulation of the oil component with certain types of polymers, such as proteins, in the presence of a solvent. For example, an article entitled "*Encapsulation of Essential Oils in Zein Nanospherical Particles*" (Parris, et al., *J. Agric. Food Chem.* 2005, 53, 4788-4792) broadly describes the encapsulation of thymol in zein nanospheres by mixing the oil with zein particles in the presence of a solvent (e.g., ethanol). The particles are said to be useful for oral or injectable administration of biological materials into the body. Another article entitled "*Controlled Release of Thymol from Zein Based Film*" (Mastromatteo, et al., *J. Innovative Food and Emerging Technologies* 2009, 10, 222-227) broadly describes films formed by dissolving corn zein and glycerol into ethanol, and thereafter adding thymol to form a solution. The solution is poured into a Petri dish and dried to form the film.

One problem with the techniques described above is that they generally rely on solvents (e.g., ethanol) to help dissolve the essential oil into a solution. A disadvantage of the use of solvents is that it puts a limit on what type of components may be employed in the composition. Additionally, solvent-based solutions require a substantial amount of time, energy, and materials for processing. Moreover, a portion of the essential oil may escape from the solution when the solvent is evaporated, which requires the use of a greater amount of oil than would normally be needed. Notwithstanding the above, the ability to use a "solventless" process in an oil and protein combination is complicated by the tendency of proteins to lose their flow properties when exposed to the intense shear and elevated temperature normally associated with melt processing. For example, proteins may undergo a conformational change ("denaturation") that causes disulfide bonds in the polypeptide to dissociate into sulfhydryl groups or thiyl radicals. Sulfhydryl groups form when disulfide bonds are chemically reduced. Thiyl radicals form when there is a mechanical scission of disulfide bonds. Once dissociated, however, free sulfhydryl groups randomly re-associate with other sulfhydryl groups to form new disulfide bond between polypeptides. Thiyl radicals can also randomly re-associate with other thiyl radicals to form new disulfide bonds or thiyl radicals may react with other amino acids to create new forms of cross-linking between polypeptides. Because one polypeptide contains multiple thiol groups, random cross-linking between polypeptide leads to formation of an "aggregated" polypeptide network, which is relatively brittle and leads to a loss of flow properties.

There lacks a method/composition to create a user saturated disinfecting wipe utilizing natural essential oils. The problem with essential oils is that they are volatile, thus when applied to substrates, loss of the essential oil from the wipe is premature resulting in a loss of efficacy before application use. In addition, there is yet another problem of utilizing essential oils for user saturated disinfecting wipe, in that because they are hydrophobic, there solubility in water is limited.

Currently, there are user saturated disinfecting wipes on the market today, such as Kimberly-Clark's WetTask® system. While these wipes are effective in their use, the user has to prepare the disinfecting solution by mixing the antimicrobial agent with water then add this solution to a nonwoven. Additionally, the antimicrobial agents are typically bleach or quants and are not viewed as environmentally friendly chemicals.

Thus, there lacks sustainable environmentally friendly technology to create user saturated disinfecting wipes that would allow users to "just add water" to the nonwoven eliminating the need for the user to mix "harsh chemicals."

SUMMARY OF THE INVENTION

A wipe suitable for multiple re-use comprising a biopolymer matrix composition, said biopolymer matrix comprising from about 0.1% to about 40% of an essential oil, about 30% to about 95% of a biopolymer, and about 1% to about 50% of a carrier fluid wherein a limited amount of said essential oil can be released from said matrix composition when exposed to a liquid solution; and wherein an additional limited amount of said essential oil can be re-released repetitiously thereafter upon re-use with an additional exposure of a liquid solution to said wipe.

DETAILED DESCRIPTION OF THE INVENTION

While the specification concludes with the claims particularly pointing out and distinctly claiming the invention, it is believed that the present invention will be better understood from the following description.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. The term "weight percent" may be denoted as "wt. %" herein. Except where specific examples of actual measured values are presented, numerical values referred to herein should be considered to be qualified by the word "about".

As used herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

As used herein, "essential oils" includes the term "botanical oils" and refers to a hydrophobic liquid that is extracted from herbs, flowers, trees, and other plants. They are typically present as tiny droplets between the cells of the plants and may be extracted by methods known to those of skill in the art (e.g., steam distillation, enfleurage (i.e., extraction using fat(s)), maceration, solvent extraction, or mechanical pressing). The essential oil of the present invention may be exact, isolated, purified or synthetically derived.

Generally speaking, the present invention is directed to a wipe comprising an environmentally friendly and effective composition wherein a functional volatile, for example, an essential oil is comprised within a biopolymer. The biopolymer serves as a matrix such that the oil is able to be released in a limited amount when exposed to a liquid solution. When released, the essential oil is able to function as an active agent that provides desired benefits unique to the oil. The composition is also typically anhydrous and generally free of solvents. In this manner, the biopolymer will not generally disperse before use and prematurely release and exhaust the full amount of essential oil at one time. Instead, the biopolymer serves as matrix to disperse only a limited amount of oil upon contact with a liquid solution such as water. Due to the limited dispersion of oil, the composition can be re-activated upon repeated, re-use and exposure to the liquid solution. The wipe is able to actively provide benefits over a prolonged period without the need to add more active for continuous and repeated use and re-use. In other words, the wipe can be used at one point of time, allowed to dry and through simple re-exposure to an aqueous solution such as water, the same wipe can be re-used. This can be repeated a number of times before the original wipe is no longer capable of delivering actives. There would be no need to re-apply an active to the wipe itself. The only thing that is needed in this example would be to add water for re-activation of the active oil within the wipe.

I. Composition

A. Functional Volatiles

Functional volatiles are employed in the composition of the present invention as actives to deliver desirable benefits. Functional volatiles can be defined as actives that provide benefit to consumers/users, including, but not limited to antimicrobial, fragrance, skin health, odor masking, soothing, aroma therapy, topical treatments, topical cooling effect, insect repellent, respiratory health, neural stimulation and other benefits. The functional volatile of the present invention may be an oil such as an essential oil that is extracted from a plant or may be non-plant derived, such as esters, fatty acids, higher alcohols, lactones, sulfurs, terpenes, and the like. Likewise, the essential oil of the present invention may also be isolated or purified from an essential oil, or it may simply be made synthetically to mimic a compound derived from a plant. Essential oils are generally soluble in lipids and are able to impart beneficial properties that are not only advantageous but are more environmentally friendly than other active compounds. For example, some essential oils are believed to exhibit antimicrobial efficacy due to their ability to cause damage to the lipid component of the cell membrane in microorganisms inhibiting their proliferation. Other benefits may also include topical cooling treatments, skin health, analgesic properties, aroma therapeutics, odor masking, reduce skin barrier function that allows for other actives to permeate through the skin (topical drug delivery), insect repellent, and the like. Additionally, one or more oils can be utilized as the active within the composition. Examples of suitable essential oils for use in the present invention may include, for instance, anise oil, lemon oil, orange oil, oregano oil, rosemary oil, wintergreen oil, thyme oil, lavender oil, clove oil, hops, tea tree oil, citronella oil, wheat oil, barley oil, lemongrass oil, cedar leaf oil, cedar wood oil, cinnamon oil, fleagrass oil, geranium oil, sandalwood oil, violet oil, cranberry oil, eucalyptus oil, vervain oil, peppermint oil, gum benzoin, basil oil, fennel oil, fir oil, balsam oil, menthol, ocmea *origanum* oil, *Hydastis carradensis* oil, *Berberidaceae daceae* oil, Ratanhiae and *Curcuma longa* oil, sesame oil, macadamia nut oil, evening primrose oil, Spanish sage oil, Spanish rosemary oil, coriander oil, pimento berries oil, rose oil, bergamot oil, rosewood oil, chamomile oil, sage oil, clary sage oil, cypress oil, sea fennel oil, frankincense oil, ginger oil, grapefruit oil, jasmine oil, juniper oil, lime oil, mandarin oil, marjoram oil, myrrh oil, neroli oil, patchouli oil, pepper oil, black pepper oil, petitgrain oil, pine oil, rose otto oil, spearmint oil, spikenard oil, vetiver oil, or ylang ylang. Still other essential oils known to those of skill in the art are also contemplated as being useful within the context of the present invention (e.g., International Cosmetic Ingredient Dictionary, $10^{th}$ and $12^{th}$ editions, 2004 and 2008, respectively, which are incorporated by reference).

In one embodiment, carvacrol and thymol-containing oils are purified from the species *Origanum vulgare* of a hirtum variety. Ideally this is a hybrid strain that produces high quality oils, but is not limited to this genus, species or strain. The oil extract may also be obtained from a plant of the genus *Nepeta* including, but not limited to species *Nepeta racemosa* (catmint), *Nepeta citriodora, Nepeta elliptica, Nepeta hindostoma, Nepeta lanceolata, Nepeta leucophylla, Nepeta longiobracteata, Nepeta mussinii, Nepeta nepetella, Nepeta sibthorpii, Nepeta subsessilis, Nepeta tuberosa, Thymus glandulosus, Thymus hyemalis, Thymus vulgaris* and *Thymus zygis*.

As indicated above, isolates and/or derivatives of essential oils may also be employed in the present invention. For example, monoterpene phenols are particularly suitable for use in the present invention, which may be isolated and purified from plant oil extracts, or made synthetically by known methods. Suitable monoterpene phenols may include, for instance, thymol, carvacrol, eucalyptol, and the like. Thymol (isopropyl-cresol) is one particularly suitable monoterpene phenol, which is a crystalline substance that has a boiling point of about 238° C. at atmospheric pressure. Carvacrol (isopropyl-o-cresol), an isomer of thymol, is another suitable compound. Carvacrol is a liquid with a boiling point of about 233° C. at atmospheric pressure. Thymol and carvacrol, as well as isomers thereof, may be derived from plant oil extracts or synthesized. For example, carvacrol may be synthesized by the reaction of nitrous acid with 1-methyl-2-amino-4-propyl benzene. In addition to being employed in an isolated or pre-synthesized form, essential oils comprising monoterpene phenols as major constituents may be employed, with the final concentrations of the monoterpene phenols being within the ranges provided herein. The term "major constituent" generally refers to those essential oils having monoterpene phenols in an amount of more than about 50 wt. %. It is well-known in the art that such essential oils may also contain lesser amounts of other constituents, such as non-aromatic terpene compounds. Essential oils with organic phenolic compounds as major constituents may include, but are not limited to, anise oil, bay oil terpineless, clove bud, clove leaf, clove oil, clove stem, *origanum* oil, Peru balsam, pimento oil, eucalyptus oil, thyme oil and mixtures thereof.

Compositions of the present invention may employ essential oils in an amount of from about 0.1 wt. % to about 40 wt. %, in some embodiments from about 0.5 wt. % to about 30 wt. %, and in some embodiments, from about 1 wt. % to about 15 wt. %.

Other functional volatiles suitable for the present invention include, but are not limited to, non-plant based volatile compounds which including, but not limited to higher alcohols, terpenes, fatty acids, sulfur containing compounds, lactones, esters, and combinations thereof.

B. Biopolymer

The composition of the present invention also comprises a biopolymer. Because essential oils are unstable, the biopolymer serves as a matrix that helps to limit the amount of oil that is released for activity. Additionally, the essential oil is inherently limited in its solubility in certain liquid solutions. The essential oil is particularly limited in its solubility in water. When a liquid solution is applied to the matrix, a limited or controlled amount of oil may be released from the matrix through various mechanisms.

First, the oil may be released from the matrix into the liquid solution via diffusion. In this case, the oil diffuses until the solubility limit of the oil is reached. The release or diffusion of the active from the matrix to the liquid solution is halted at the solubility limit and the remaining active oil ingredient stays entrapped within the biopolymer matrix until the time of re-use. Upon re-use, a new liquid solution can then be re-applied allowing for an additional limited amount of remaining active compound to be released again from the biopolymer matrix into solution. This process can be repeated multiple times allowing for multiple releases of actives from the biopolymer matrix. Through this mechanism, it is known that a limited amount is release because not the entire biopolymer matrix disperses or dissolve in the added liquid. When the biopolymer and active are extruded, an agglomerated/compacted composition is formed. Thus when liquid is added to the material it will not completely dispersion or dissolve right away. The amount of biopolymer that dissolves or disperses from the matrix is dependent on time. The amount of time needed for dispersal of such polymers so that they release the desired benefits of the active will depend at least in part upon the particular end-use design criteria. In most embodiments, the matrix will begin to disperse and release the essential oil active generally within about 5 minutes, within about 1 minute, within about 30 seconds, or within about 10 seconds.

Another mechanism that allows multiple release of active is by dispersing or dissolving the outer biopolymer matrix. When the liquid solution comes into contact with the biopolymer matrix, the biopolymer at the surface can dissolve or disperse into solution. As this dispersion or dissolving occurs, the active component is simultaneously released into the liquid solution as well. The active is release into solution because it is homogeneously mixed within the biopolymer matrix. So as the biopolymer matrix disperses or dissolves into solution so does the active component. To help control the amount of active that is released during the initial liquid solution contact, the dispersability or solubility of biopolymer within the liquid solution may be changed so that as the biopolymer becomes more dispersible or soluble in the liquid solution, larger amounts of biopolymer will disperse or dissolve in the liquid which, allows for a greater amount of active to be released. Alternatively, as the biopolymer becomes less dispersible or soluble in the liquid solution, less active is released. The biopolymer can also act as an emulsifier which facilitates concentrations of the active in the liquid solution above the active's solubility limit. The biopolymer does so by interacting its hydrophilic component with the hydrophilic solution, while interacting its hydrophobic component with the hydrophobic essential oil. For example, when proteins are used as the biopolymer, the hydrophilic based amino acid side chains interact with hydrophilic liquid, while the hydrophobic amino acid side chains interact with hydrophobic functional volatile.

Material surface area to volume ratio can also be utilized to control the multiple release of actives from the composition matrix. The greater the surface area, the greater the contact area is for the liquid solution. This greater amount of contact surface area allows for more actives to be released or biopolymer to disperse or dissolve into the liquid solution. In reverse, as surface area decreases to volume, the amount of contact area between particles and liquid decreases thereby decreasing the amount of active release and/or biopolymer dispersed. Surface area to volume ratio, thus, can be utilized to control the amount and number of time an active can be released. The biopolymer matrix can be in a variety of forms including, but not limited to, nonwoven webs, pellets, films, fibers, molded parts (such as injection molding and the like), particles/powders. Biopolymers suitable for the present invention include, but are not limited to, proteins, starches, cellulose, and combinations thereof. Biopolymers can be utilized in their native state or may be modified for particular applications. Chemical modifications can be utilized to control the dispersability or solubility of the biopolymer within the application liquid. This indirect modification allows controlling the release amount of the active. In addition, such modifications can include cross-linking.

a. Proteins

Proteins used as biopolymers of the present invention include, but are not limited to, vegetable proteins, dairy proteins, animal proteins, as well as concentrates or isolates thereof. The protein source may be, for instance, milk (e.g., casein or caeseinates), whey, corn (e.g., zein), wheat (e.g., wheat gluten), soy, or other vegetable or animal sources. Plant proteins are particularly suitable for use in the present invention, such as zein, corn gluten, wheat gluten, whey protein, soy protein, etc. Any form of protein may be used, such as isolates, concentrates and flour. For example, soy proteins may be in the form of an isolate containing from about 75 wt. % to about 98 wt. % protein, a concentrate containing from about 50 wt. % to about 75 wt. % protein, or flour containing from about 30 wt. % to about 50 wt. % protein. In certain embodiments, it is desirable to use a protein that is relatively pure, such as those having a protein content of about 75 wt. % or more, and in some cases, about 85 wt. % or more. Gluten proteins, for instance, may be purified by washing away any associated starch to leave a composite of gliadin and glutenin proteins. In one particular embodiment, a vital wheat gluten is employed. Such vital wheat gluten is commercially available as a creamy-tan powder produced from wheat flour by drying freshly washed gluten. For instance, vital wheat gluten can be obtained from Archer Daniels Midland ("ADM") of Decatur, Ill. under the designations WhetPro® 75 or 80. Similarly, purified soy protein isolates may be prepared by alkaline extraction of a defatted meal and acid precipitation, a technique well-known and used routinely in the art. Such purified soy proteins are commercially available from ADM under the designation PRO-FAM®, which typically have a protein content of 90 wt. % or more. Other purified soy protein products are also available from DuPont of Louisville, Ky.

under the designation PRO-COTE® and from Central Soya under the designation Promie R.

If desired, the protein may also be modified using techniques known in the art to improve its ability to disperse in an aqueous solution, which may be applied to the composition to release the essential oil during and/or just prior to use as described in more detail below. Suitable modification techniques may include pH modification, denaturation, hydrolysis, acylation, reduction, oxidation, etc. Just as an example, gluten may sometimes absorb water until it begins to repel excess water. This results in gluten molecules that are associated closely together such that they resist dispersion in aqueous solutions. To counteract this tendency, the protein may be treated with a pH modifier to increase its solubility in aqueous environments. Typically, the pH modifier is a basic reagent that can raise the pH of the protein, thereby causing it to become more soluble in aqueous solutions. Monovalent cation-containing basic reagents (hereafter "monovalent basic reagents") are particularly suitable for use in the present invention. Examples of such monovalent basic reagents include, for instance, alkali metal hydroxides (e.g., sodium hydroxide, ammonium hydroxide, etc.), ammonia, etc. Of course, multivalent reagents, such as alkaline metal hydroxides (e.g., calcium hydroxide) and alkaline metal oxides (e.g., calcium oxide), may also be employed if desired. When employed, the pH modifier may be present in an amount such that the pH of the protein is from about 7 to about 14, and in some embodiments, from about 8 to about 12.

Hydrolysis of the protein material may also improve water solubility, and can be affected by treating the protein with a hydrolytic enzyme. Many enzymes are known in the art which hydrolyze protein materials, including, but not limited to, proteases, pectinases, lactases, and chymotrypsin. Enzyme hydrolysis is affected by adding a sufficient amount of enzyme to an aqueous dispersion of protein material, typically from about 0.1% to about 10% enzyme by weight of the protein material, and treating the enzyme and protein dispersion. After sufficient hydrolysis has occurred the enzyme may be deactivated by heating, and the protein material may be precipitated from the solution by adjusting the pH of the solution to about the isoelectric point of the protein material.

The composition of the present invention typically employs proteins in an amount of from about 30 wt. % to about 95 wt. %, in some embodiments from about 40 wt. % to about 90 wt. %, and in some embodiments, from about 50 wt. % to about 80 wt. %.

b. Starches or Carbohydrates

The biopolymer utilized in the present invention can also contain a modified starch. Because the essential oil tends to leach out during storage and before it is used in the desired application, the modified starch polymer helps enhance the long term stability of the oil and, in turn, the efficacy of the desired benefits thereof. Without intending to be limited by theory, it is believed that the physical structure of the starch can effectively encapsulate the essential oil and inhibit/control its premature release. Nevertheless, when it is desired to release the essential oil prior to and/or during use, the modified starch can disperse (e.g., disintegrate, dissolve, change physical form, etc.) when placed in an aqueous environment as described above.

Although starch polymers are produced in many plants, typical sources includes seeds of cereal grains, such as corn, waxy corn, wheat, sorghum, rice, and waxy rice; tubers, such as potatoes; roots, such as tapioca (i.e., cassava and manioc), sweet potato, and arrowroot; and the pith of the sago palm. Regardless of its source, the starch is modified so that it possesses a higher degree of water sensitivity, which helps facilitate degradation upon contact with water. Such modified starches may be obtained through typical processes known in the art (e.g., esterification, etherification, oxidation, acid hydrolysis, enzymatic hydrolysis, and the like.). In another embodiment, the starch is modified so that it possesses a low degree of water sensitivity, which helps facilitate a lower degree of essential oil release.

Starch ethers and/or esters are particularly desirable, such as hydroxyalkyl starches. Without intending to be limited by theory, it is believed that such modified starches possess polar groups (e.g., hydroxy) and nonpolar groups (e.g., alkyl) that are capable of interacting with the polar (e.g., phenolic hydroxyl) and nonpolar (e.g., isopropyl) groups, respectively, found in monoterpene phenolic botanical oils. This enhances the ability of the starch polymer to trap and hold the botanical oil prior to use. Furthermore, the modification of the starch polymer provides enhanced chain flexibility, which even further enhances its trapping efficiency. The hydroxyalkyl group of hydroxylalkyl starches may contain, for instance, 2 to 10 carbon atoms, in some embodiments from 2 to 6 carbon atoms, and in some embodiments, from 2 to 4 carbon atoms. Representative hydroxyalkyl starches such as hydroxyethyl starch, hydroxypropyl starch, hydroxybutyl starch, and derivatives thereof. Starch esters, for instance, may be prepared using a wide variety of anhydrides (e.g., acetic, propionic, butyric, and so forth), organic acids, acid chlorides, or other esterification reagents. The degree of esterification may vary as desired, such as from 1 to 3 ester groups per glucosidic unit of the starch. Other types of modified starches can be employed in the present invention that is known the art, such as cationic, anionic, crosslinked, oxidized, and enzyme-catalyzed.

The starch polymer may contain different weight percentages of amylose and amylopectin, different polymer molecular weights, etc. High amylose starches contain greater than about 50% by weight amylose and low amylose starches contain less than about 50% by weight amylose. Although not required, low amylose starches having an amylose content of from about 10% to about 40% by weight, and in some embodiments, from about 15% to about 35% by weight, are particularly suitable for use in the present invention. Examples of such low amylose starches include corn starch and potato starch, both of which have an amylose content of approximately 20% by weight. Particularly suitable low amylose starches are those having a number average molecular weight ("Mn") ranging from about 50,000 to about 1,000,000 grams per mole, in some embodiments from about 75,000 to about 800,000 grams per mole, and in some embodiments, from about 100,000 to about 600,000 grams per mole, and/or a weight average molecular weight ("Mw") ranging from about 5,000,000 to about 25,000,000 grams per mole, in some embodiments from about 5,500,000 to about 15,000,000 grams per mole, and in some embodiments, from about 6,000,000 to about 12,000,000 grams per mole. The ratio of the weight average molecular weight to the number average molecular weight ("Mw/Mn"), i.e., the "polydispersity index", is also relatively high. For example, the polydispersity index may range from about 10 to about 100, and in some embodiments, from about 20 to about 80. The weight and number average molecular weights may be determined by methods known to those skilled in the art.

The composition of the present invention typically employs modified starch polymers in an amount of from about 30 wt. % to about 95 wt. %, in some embodiments from about 40 wt. % to about 90 wt. %, and in some embodiments, from about 50 wt. % to about 80 wt. %.

C. Carrier Fluid

A carrier fluid may also be employed in the composition of the present invention to help render the protein and/or starch more flowable under melt processing conditions and allow it to receive the essential oil within its internal structure. Suitable carrier fluids may include, but are not limited to, polyhydric alcohols, such as sugars (e.g., glucose, sucrose, fructose, raffinose, maltodextrose, galactose, xylose, maltose, lactose, mannose, and erythrose), sugar alcohols (e.g., erythritol, xylitol, malitol, mannitol, and sorbitol), polyols (e.g., ethylene glycol, glycerol, propylene glycol, dipropylene glycol, butylene glycol, and hexane triol), and the like. Also suitable are hydrogen bond forming organic compounds which do not have hydroxyl group, including urea and urea derivatives; anhydrides of sugar alcohols such as sorbitan; animal proteins such as gelatin; vegetable proteins such as sunflower protein, soybean proteins, cotton seed proteins; and mixtures thereof. Additionally phthalate esters, dimethyl and diethylsuccinate and related esters, glycerol triacetate, glycerol mono and diacetates, glycerol mono, di, and tripropionates, butanoates, stearates, lactic acid esters, citric acid esters, adipic acid esters, stearic acid esters, oleic acid esters, and other acid esters may be used. Aliphatic carboxylic acids may also be used, such as lactic acid, maleic acid, acrylic acid, copolymers of ethylene and acrylic acid, polyethylene grafted with maleic acid, polybutadiene-co-acrylic acid, polybutadiene-co-maleic acid, polypropylene-co-acrylic acid, polypropylene-co-maleic acid, and other hydrocarbon based acids. A low molecular weight carrier fluid is preferred, such as those that are less than about 20,000 g/mol, less than about 5,000 g/mol or less than about 1,000 g/mol.

If desired, the carrier fluid may be selected to have a certain pH (refers to the pH prior to incorporation into the composition). For example, carrier fluids having a relatively low pH can reduce the tendency of gluten proteins to aggregate during melt processing. Thus, when gluten proteins are employed, a carrier fluid may be selected that has a pH of about 6 or less, in some embodiments from about 1 to about 5, and in some embodiments, from about 2 to about 4. Examples of such carrier fluids may include, but are not limited to, aliphatic carboxylic acids, such as lactic acid, maleic acid, acrylic acid, and the like. In other embodiments, it may be desirable to use carrier fluids having a higher pH, such as when the plant protein is not generally sensitive to pH. For example, soy proteins generally lack the cysteine residues that lead to aggregation in gluten proteins. Thus, when employed, the soy protein may be used with carrier fluids having a relatively wide range of pH levels. One example of such a carrier fluid is glycerol, which has a pH of about 6.

The amount of the carrier fluids employed depends in part on the nature of the selected essential oil and protein and may or may not be employed within the present invention. Carrier fluids are included at levels of from about 0%, or from about 5% or from about 10% to about 50%, or to about 30%, or to about 20%, by weight of the composition.

D. Other Components

Additives may be incorporated into the composition by adding them to the active oil particles. Additives function to control the multiple release mechanism of the present invention. These additives could also facilitate concentrations of active into solution above its solubility limit. Such an example includes incorporating surfactants into the particle to help release the active into the liquid solution above its solubility limit. If the active is hydrophobic and the liquid solution is hydrophilic, then addition of an additive such as a surfactant or combination thereof could help facilitate the release of the hydrophobic active in the hydrophilic liquid. Other additives or components include pigments, inorganic fillers, and processing aides.

II. Processing

The natural, biopolymer and essential oil compositions that have the capability to release actives multiple times are created via melt processing. The active is melt incorporated into the biopolymer matrix via extrusion or other melt processes. The resulting extruded strand is downsized to a particle size of choice. Particle sizes may be from about 1 micrometers to about 10000 micrometers, from about 30 micrometers to about 2000 micrometers, or from about 100 micrometers to 500 micro meters. The downsized particles can then be applied to a substrate such as a nonwoven material to create a semi-durable use wipe that disperses the desired benefit of the active oil. Other means to apply the melt process material could also be applied to this invention, which may include forming fibers or films and applying these fibers or films to nonwoven materials.

Downsizing of the extruded material can be carried out through known techniques in the art. Such downsizing methods/equipment includes but is not limited to micro pelletization, disk milling, attrition milling, granulators, grinders, rotary cutters, shredders, cryogenic grinders, solid-state shear pulverization, hammermills, impact mills, ball mills, and the like.

Despite the problems normally associated with melt processing proteins, the present inventors have discovered that the processing conditions and components may be selectively controlled to allow for the formation of a stable, melt-processed composition that is able to exhibit good mechanical properties. For example, the extrusion temperature(s) and shear rate employed during melt blending are relatively low to help limit polypeptide dissociation, thereby minimizing the impact of aggregation and embrittlement. While the use of such low temperature/shear conditions often tend to reduce mixing efficiency, the carrier fluid of the present invention may be employed to enhance the ability of the essential oil to flow into the internal structure of the protein where it can be retained until activated for release.

III. Substrates

The matrix composition may be applied to or embedded within a wide variety of different articles for imparting benefits. In one particular embodiment, the composition is applied to a wipe. Such wipes may be used to reduce microbial or viral populations on a hard surface (e.g., sink, table, counter, sign, and so forth) or surface on a user/patient (e.g., skin, mucosal membrane, such as in the mouth, nasal passage, stomach, vagina, etc., wound site, surgical site, and so forth). The wipe may provide an increased surface area to facilitate contact of the composition with microorganisms. In addition, the wipe may also serve other purposes, such as providing water absorption, barrier properties, etc. The wipe may also eliminate microorganisms through frictional forces imparted to the surface.

The wipe may be formed from any of a variety of materials as is well known in the art. Typically, however, the wipe includes a fibrous web that contains absorbent fibers. For example, the wipe may be a paper product containing one or more paper webs, such as facial tissue, bath tissue, paper towels, napkins, and so forth. The paper product may be single-ply in which the web forming the product includes a single layer or is stratified (i.e., has multiple layers), or multi-ply, in which the webs forming the product may themselves be either single or multi-layered. Normally, the basis weight of such a paper product is less than about 120 grams per square meter ("gsm"), in some embodiments less than about 80 gsm, in some embodiments less than about 60 grams per square meter, and in some embodiments, from about 10 to about 60 gsm. Any of a variety of materials can also be used to form the paper web(s) of the product. For example, the material used to make the paper product may include absorbent fibers formed by a variety of pulping processes, such as kraft pulp, sulfite pulp, thermomechanical pulp, etc. The pulp fibers may include softwood fibers having an average fiber length of greater than 1 mm and particularly from about 2 to 5 mm based on a length-weighted average. Such softwood fibers can include, but are not limited to, northern softwood, southern softwood, redwood, red cedar, hemlock, pine (e.g., southern pines), spruce (e.g., black spruce), combinations thereof, and so forth. Exemplary commercially available pulp fibers suitable for the present invention include those available from Kimberly-Clark Corporation under the trade designations Longlac-19®. Hardwood fibers, such as eucalyptus, maple, birch, aspen, and so forth, can also be used. In certain instances, eucalyptus fibers may be particularly desired to increase the softness of the web. Eucalyptus fibers can also enhance the brightness, increase the opacity, and change the pore structure of the web to increase its wicking ability. Moreover, if desired, secondary fibers obtained from recycled materials may be used, such as fiber pulp from sources such as, for example, newsprint, reclaimed paperboard, and office waste. Further, other natural fibers can also be used in the present invention, such as abaca, sabai grass, milkweed floss, pineapple leaf, bamboo, algae, and so forth. In addition, in some instances, synthetic fibers can also be utilized.

If desired, the absorbent fibers (e.g., pulp fibers) may be integrated with synthetic fibers to form a composite. Synthetic thermoplastic fibers may also be employed in the nonwoven web, such as those formed from polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; polyhydroxyalkanoate; copolymers thereof; and so forth. Because many synthetic thermoplastic fibers are inherently hydrophobic (i.e., non-wettable), such fibers may optionally be rendered more hydrophilic (i.e., wettable) by treatment with a surfactant solution before, during, and/or after web formation. Other known methods for increasing wettability may also be employed, such as described in U.S. Pat. No. 5,057,361 to Sayovitz, et al. The relative percentages of such fibers may vary over a wide range depending on the desired characteristics of the composite. For example, the composite may contain from about 1 wt. % to about 60 wt. %, in some embodiments from 5 wt. % to about 50 wt. %, and in some embodiments, from about 10 wt. % to about 40 wt. % synthetic polymeric fibers. The composite may likewise contain from about 40 wt. % to about 99 wt. %, in some embodiments from 50 wt. % to about 95 wt. %, and in some embodiments, from about 60 wt. % to about 90 wt. % absorbent fibers.

Composites, such as described above, may be formed using a variety of known techniques. For example, a nonwoven composite may be formed that is a "coform material" that contains a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al. Alternatively, the nonwoven composite may be formed be formed by hydraulically entangling staple length fibers and/or filaments with high-pressure jet streams of water. Various techniques for hydraulically entangling fibers are generally are disclosed, for example, in U.S. Pat. No. 3,494,821 to Evans and U.S. Pat. No. 4,144,370 to Bouolton. Hydraulically entangled nonwoven composites of continuous filaments (e.g., spunbond web) and natural fibers (e.g., pulp) are disclosed, for example, in U.S. Pat. No. 5,284,703 to Everhart, et al. and U.S. Pat. No. 6,315,864 to Anderson, et al. Hydraulically entangled nonwoven composite of staple fiber blends (e.g., polyester and rayon) and natural fibers (e.g., pulp), also known as "spunlaced" fabrics, are described, for example, in U.S. Pat. No. 5,240,764 to Haid, et al.

Regardless of the materials or processes utilized to form the wipe, the basis weight of the wipe is typically from about 20 to about 200 grams per square meter ("gsm"), and in some embodiments, between about 35 to about 100 gsm. Lower basis weight products may be particularly well suited for use as light duty wipes, while higher basis weight products may be better adapted for use as industrial wipes.

The wipe may assume a variety of shapes, including but not limited to, generally circular, oval, square, rectangular, or irregularly shaped. Each individual wipe may be arranged in a folded configuration and stacked one on top of the other to provide a stack of wet wipes. Such folded configurations are well known to those skilled in the art and include c-folded, z-folded, quarter-folded configurations and so forth. For example, the wipe may have an unfolded length of from about 2.0 to about 80.0 centimeters, and in some embodiments, from about 10.0 to about 25.0 centimeters. The wipes may likewise have an unfolded width of from about 2.0 to about 80.0 centimeters, and in some embodiments, from about 10.0 to about 25.0 centimeters. The stack of folded wipes may be placed in the interior of a container, such as a plastic tub, to provide a package of wipes for eventual sale to the consumer. Alternatively, the wipes may include a continuous strip of material which has perforations between each wipe and which may be arranged in a stack or wound into a roll for dispensing. Various suitable dispensers, containers, and systems for delivering wipes are described in U.S. Pat. No. 5,785,179 to Buczwinski, et al.; U.S. Pat. No. 5,964,351 to Zander; U.S. Pat. No. 6,030,331 to Zander; U.S. Pat. No. 6,158,614 to Haynes, et al.; U.S. Pat. No. 6,269,969 to Huang, et al.; U.S. Pat. No. 6,269,970 to Huang, et al.; and U.S. Pat. No. 6,273,359 to Newman, et al.

The composition may be incorporated into the wipe in a variety of different ways. For example, the composition may be applied to a surface of the wipe using known techniques, such as printing, dipping, spraying, melt extruding, coating (e.g., solvent coating, powder coating, brush coating, etc.), foaming, and so forth. If desired, the composition may be applied in a pattern that covers from about 5% to about 95%, in some embodiments from about 10% to about 90%, and in some embodiments, from about 20% to about 75% of a surface of the wipe. Such patterned application may have various benefits, including enhanced aesthetic appeal, improved absorbency, etc. The particular type or style of the pattern is not a limiting factor of the invention, and may include, for example, any arrangement of stripes, bands, dots, or other geometric shape. The pattern may include indicia (e.g., trademarks, text, and logos), floral designs, abstract designs, any configuration of artwork, etc. It should be appreciated that the "pattern" may take on virtually any desired appearance. The composition may also be blended with the fibers used to form the wipe. This may be particularly useful when the composition is in the form of particles. For example, such particles may be blended with the absorbent fibers (e.g., pulp fibers, staple fibers, etc.) during hydraulic entanglement, coforming, etc. The particles may also be incorporated into the thermoplastic material of the wipe (e.g., meltblown web) using known techniques.

The amount of the composition on the wipe may vary depending on the nature of the substrate and its intended application. For example, the add-on level of the composition may be from about 5% to about 100%, in some embodiments from about 10% to about 80%, and in some embodiments, from about 20% to about 70%. The "add-on level" is determined by subtracting the weight of the untreated substrate from the weight of the treated substrate, dividing this calculated weight by the weight of the untreated substrate, and then multiplying by 100%. Lower add-on levels may provide optimum functionality of the substrate, while higher add-on levels may provide optimum antimicrobial efficacy.

To use the composition, an aqueous solution may simply be added, thereby dispersing the starch and releasing the botanical oil. The aqueous solution may contain only water, or it may contain water in combination with other components. For example, a weak acid may be employed to help disperse the starch and facilitate the release of the oil upon contact with the aqueous solution. Suitable acids for this purpose may include, for instance, organic carboxylic acids, such as citric acid, oxalic acid, lactic acid, acetic acid, etc. Regardless, the present inventors have surprisingly discovered that the amount of the botanical oil released into the aqueous solution can be even greater than the normal solubility limit of the oil in water. Without intending to be limited by theory, it is believed that this can be achieved because the physical structure of the starch is able to effectively "carry" the volatile into the released solution. For example, the solubility limit of thymol in water (at 25° C.) is typically about 0.1 wt. %. When released from the composition of the present invention, however, the concentration of thymol in the released solution can be greater than about 0.1 wt. %, in some embodiments greater than about 0.15 wt. %., in some embodiments from about 0.2 wt. % to about 10 wt. %, and in some embodiments, from about 0.2 wt. % to about 4 wt. %.

The present inventors have discovered that the composition of the present invention may inhibit (e.g., reduce by a measurable amount or to prevent entirely) the growth of one or more microorganisms when exposed thereof. Examples of microorganisms that may be inhibited include bacteria, protozoa, algae, and fungi (e.g., molds and yeast). Furthermore is possible to use this invention to inactivate viruses, prions and other infectious particles. For example, the composition may inhibit the growth of several medically significant bacteria groups, such as Gram negative rods (e.g., *Entereobacteria*); Gram negative curved rods (e.g., *Helio-bacter, Campylobacter*, etc.); Gram negative cocci (e.g., *Neisseria*); Gram positive rods (e.g., *Bacillus, Clostridium*, etc.); Gram positive cocci (e.g., *Staphylococcus, Streptococcus*, etc.); obligate intracellular parasites (e.g., *Ricckettsia* and *Chlamydia*); acid fast rods (e.g., *Myobacterium, Nocardia*, etc.); spirochetes (e.g., *Treponema, Borellia*, etc.); and mycoplasmas (i.e., tiny bacteria that lack a cell wall). Particularly species of bacteria that may be inhibited with the composition of the present invention include *Escherichia coli* (Gram negative rod), *Klebsiella pneumonia* (Gram negative rod), *Streptococcus* (Gram positive cocci), *Salmonella choleraesuis* (Gram negative rod), *Staphyloccus aureus* (Gram positive cocci), and *P. aeruginosa* (Gram negative rod). In addition to bacteria, other microorganisms of interest include fungi (e.g., *Aspergillus niger*) and yeasts (e.g., *Candida albicans*).

Upon exposure for a certain period of time, the composition may provide a log reduction of at least about 2, in some embodiments at least about 3, in some embodiments at least about 4, and in some embodiments, at least about 5 (e.g., about 6). Log reduction, for example, may be determined from the % population killed by the composition according to the following correlations:

| % Reduction | Log Reduction |
|---|---|
| 90 | 1 |
| 99 | 2 |
| 99.9 | 3 |
| 99.99 | 4 |
| 99.999 | 5 |
| 99.9999 | 6 |

Such a log reduction may be achieved in accordance with the present invention after only a relatively short exposure time. For example, the desired log reduction may be achieved after exposure for only 30 minutes, in some embodiments 15 minutes, in some embodiments 10 minutes, in some embodiments 5 minutes, in some embodiments 1 minute, and in some embodiments, 30 seconds.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Example 1

A wipe that releases thymol multiple times with addition and removal of water is provided. A "PRISM USALAB 16" lab scale twin screw extruder was employed to melt process WhetPro® 75 vital wheat gluten from Archer Daniels Midland, Emery 917 Glycerin 99.7% USP, Kosher from Emery Oleochemicals LLC, and thymol≥99.% from Sigma-Aldrich. The extruder contained eleven (11) different zones, although zones 1 through 5, and 11 were not utilized in this Example. The extruder was used with a 0.75-inch die system (zone 11) to allow for ease of material to exit extruder. The gluten and thymol were pre-blended (83 wt % gluten and 17 wt % thymol) and subsequently added to the extruder at zone 6 at a feed rate of 0.5 lbs./hr. Glycerine was then added at zone 7 at a feed rate of 0.087 lbs./hr. to give an approximate composition of 71% WhetPro®, 14% glycerol, 15% thymol.

The screw configuration was composed of conveying elements at zones 6 and 7, kneading blocks at zones 8 and 9, and conveying elements at zone 10. The screw speed was 50 rpm. The temperature profile for zones 9-11 was 70° C. The resulting material was contained in plastic bag and stored at −32° C. Cooled material was downsized via Brickmann/Retsch lab scale grinding mill (set speed=1). Particles less than 425 μm were removed by sieving. The ≥425 μm particles were secured between two 6 inch by 6 inch Wypall® Hydroknit X60® sheets via ultrasonic bonding. Loading level of the particles was 50 wt. % to the weight of the two 6 inch by 6 inch Wypall® Hydroknit X60® sheets. Deionized water (DI water) was added at 375 wt. % to the weight of the particle containing wipe, waited 5 minutes before expressing solution into glass vial. Wet wipe was allowed to dry for approximately 60 minutes. Added 375 wt. %, waited 5 minutes, expressed and dried for 60 minutes were repeated to collect a total of 5 expression samples from one wipe. Thymol in expression was quantified via high performance liquid chromatography. Results are set forth in Table 1.

TABLE 1

Multiple Releases of Thymol from Gluten containing Wipe

| Expression | Thymol wt. % in Expression Solution |
| --- | --- |
| $1^{st}$ Expression | 0.021 |
| $2^{nd}$ Expression | 0.017 |
| $3^{rd}$ Expression | 0.018 |
| $4^{th}$ Expression | 0.016 |
| $5^{th}$ Expression | 0.017 |

Example 2

A wipe that release thymol multiple times with the addition and removal of water is demonstrated. Hydroxypropyl starch phosphate called Structure® XL from Akzo Nobel, Emery 917 Glycerin 99.7% USP, Kosher from Emery Oleochemicals LLC, and thymol≥99.% from Sigma-Aldrich were blended together via Kitchen Aide mixer at percentages of 80 wt. %, 15 wt. %, and 5 wt. % respectively. The resulting blend was starve fed into zone 1 of "PRISM USALAB 16" lab scale twin screw extruder at a feed rate of 0.75 lbs./hr. Temperature profile for zones 2-11 were 85° C., 95° C., 102° C., 115° C., 128° C., 123° C., 117° C., 114° C., 104° C., 96° C. respectively. Screw speed was 200 rpm. Temperature zone 11 was 3 mm strand die. The extruded strand was pelletized, and downsized via Brickmann/Retch lab scale grinding mill (set speed=1) and sieved to collect particles with size range from 250-425 μm. The resulting particles were secured between two 6 inch by 6 inch Wypall® Hydroknit X60® sheets via ultrasonic bonding. Loading level of the particles were 50 wt. % to the weight of the two 6 inch by 6 inch Wypall® Hydroknit X60® sheets. Deionized water (DI water) was added at 375 wt. % to the weight of the particle containing wipe, waited 5 minutes before expressing solution into a glass vial. Wet wipe was allowed to dry for approximately 60 minutes. Adding 375 wt. %, waiting 5 minutes, expressed and dried for 60 minutes were repeated to collect a total of 5 expression samples from one wipe. Thymol in expression solution was quantified via high performance liquid chromatography. Results are set forth in Table 2.

TABLE 2

Multiple Releases of Thymol from Starch containing Wipe

| Expression | Thymol wt. % in Expression Solution |
| --- | --- |
| $1^{st}$ Expression | 0.151 |
| $2^{nd}$ Expression | 0.040 |
| $3^{rd}$ Expression | 0.026 |
| $4^{th}$ Expression | 0.004 |
| $5^{th}$ Expression | 0.004 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wipe suitable for multiple re-use comprising a melt-processed biopolymer matrix composition, the biopolymer matrix comprising from about 0.1% to about 40% of an essential oil, about 30% to about 95% of a biopolymer, and about 1% to about 50% of a carrier fluid, wherein the wipe further comprises a fibrous material.

2. The wipe of claim 1 wherein the essential oil comprises a monoterpene phenol selected from thymol, carvacrol, and mixtures thereof.

3. The wipe of claim 1 wherein the essential oil is thymol.

4. The composition of claim 1 wherein the biopolymer is selected from proteins, starches, cellulose, and mixtures thereof.

5. The wipe of claim 4 wherein the protein is selected from soy, wheat gluten, and mixtures thereof.

6. The wipe of claim 5 wherein the protein is wheat gluten.

7. The wipe of claim 1 wherein the carrier fluid is selected from polyhydric alcohols, aliphatic carboxylic acids, and mixtures thereof.

8. The wipe of claim 1 wherein the carrier fluid is less than about 20,000 g/mol.

9. The wipe of claim 6 wherein the carrier fluid has a pH of about 6 or less.

10. The wipe of claim 5 wherein the protein is soy protein.

11. The wipe of claim 10 wherein the carrier fluid is glycerol with a pH of about 6.

12. The wipe of claim 1 wherein the essential oil is released in a controlled amount through mechanisms selected from interaction with the liquid solution, dissolution of the biopolymer matrix, adjusting the surface area to volume ratio, and combinations thereof.

* * * * *